United States Patent
Radhakrishnan et al.

(10) Patent No.: US 11,911,145 B2
(45) Date of Patent: Feb. 27, 2024

(54) METHODS AND SYSTEMS FOR DETERMINING COLLATERAL VENTILATION

(71) Applicant: Pulmonx Corporation, Redwood City, CA (US)

(72) Inventors: Sri Radhakrishnan, Cupertino, CA (US); Ryan Olivera, Granite Bay, CA (US)

(73) Assignee: Pulmonx Corporation, Redwood City, CA (US)

( * ) Notice: Subject to any disclaimer, the term of this patent is extended or adjusted under 35 U.S.C. 154(b) by 123 days.

(21) Appl. No.: 17/363,667

(22) Filed: Jun. 30, 2021

(65) Prior Publication Data

US 2022/0007967 A1  Jan. 13, 2022

Related U.S. Application Data

(60) Provisional application No. 63/050,632, filed on Jul. 10, 2020.

(51) Int. Cl.
*A61B 5/091* (2006.01)
*A61B 5/00* (2006.01)

(52) U.S. Cl.
CPC ............ *A61B 5/091* (2013.01); *A61B 5/6853* (2013.01); *A61B 5/742* (2013.01); *A61B 5/4836* (2013.01)

(58) Field of Classification Search
CPC ..... A61B 5/091; A61B 5/6853; A61B 5/6852; A61B 5/097; A61B 5/08
See application file for complete search history.

(56) References Cited

U.S. PATENT DOCUMENTS

| | | |
|---|---|---|
| 7,798,147 B2 | 9/2010 | Hendricksen et al. |
| 7,883,471 B2 | 2/2011 | Aljuri et al. |
| 8,136,526 B2 | 3/2012 | Perkins et al. |
| 10,758,239 B2 | 9/2020 | Aljuri et al. |

(Continued)

FOREIGN PATENT DOCUMENTS

| WO | WO-2006078451 A2 | 7/2006 |
| WO | WO-2009135070 A1 | 11/2009 |
| WO | WVO-2022010722 A1 | 1/2022 |

OTHER PUBLICATIONS

PCT/US2021/040000 International Search Report and Written Opinion of the International Searching Authority dated Oct. 19, 2021.

(Continued)

*Primary Examiner* — Eric F Winakur
*Assistant Examiner* — Elina Sohyun Ahn
(74) *Attorney, Agent, or Firm* — Kilpatrick Townsend & Stockton LLP

(57) ABSTRACT

Methods and systems for determining collateral ventilation are disclosed. Methods may comprise introducing a diagnostic catheter into a lung compartment via an assisted ventilation device, inflating the occluding member to isolate the lung compartment, and performing a diagnostic procedure with the catheter while the patient is ventilated via the assisted ventilation device. The diagnostic procedure comprises determining an exhaled volume from the isolated lung compartment over a predetermined period of time while the patient is ventilated via the assisted ventilation device. The presence collateral ventilation may be determined based on the exhaled volume from the isolated lung compartment over the predetermined period of time.

20 Claims, 4 Drawing Sheets

(56) References Cited

U.S. PATENT DOCUMENTS

| | | |
|---|---|---|
| 2002/0049370 A1 | 4/2002 | Laufer et al. |
| 2003/0051733 A1 | 3/2003 | Kotmel et al. |
| 2007/0142742 A1 | 6/2007 | Aljuri et al. |
| 2008/0027343 A1 | 1/2008 | Fields et al. |
| 2011/0270116 A1 | 11/2011 | Freitag et al. |
| 2014/0336484 A1 | 11/2014 | Mantri et al. |
| 2018/0353116 A1 | 12/2018 | Mantri et al. |

OTHER PUBLICATIONS

Koster et al., "An adjusted and time-saving method to measure collateral ventilation with Chartis", ERJ Open Research, 2021, pp. 1-8.

METHODS AND SYSTEMS FOR DETERMINING COLLATERAL VENTILATION

CROSS-REFERENCE TO RELATED APPLICATIONS

This application claims the benefit of U.S. Provisional No. 63/050,632, filed Jul. 10, 2020, the entire content of which are incorporated herein by reference.

BACKGROUND OF THE INVENTION

1. Field of the Invention. This invention relates generally to methods for diagnosis and treatment of lung disease.

Chronic obstructive pulmonary disease (COPD), including emphysema and chronic bronchitis, is a significant medical problem currently affecting around 16 million people in the U.S. alone (about 6% of the U.S. population). In general, two types of diagnostic tests are performed on a patient to determine the extent and severity of COPD: 1) imaging tests; and 2) functional tests. Imaging tests, such as chest x-rays, computerized tomography (CT) scans, Magnetic Resonance Imaging (MM) images, perfusion scans, and bronchograms, provide a good indicator of the location, homogeneity and progression of the diseased tissue. However, imaging tests do not provide a direct indication of how the disease is affecting the patient's overall lung function and respiration. Lung function can be better assessed using functional testing, such as spirometry, plethysmography, oxygen saturation, and oxygen consumption stress testing, among others. Together, these imaging and functional diagnostic tests are used to determine the course of treatment for the patient.

One of the emerging treatments for COPD involves the endoscopic introduction of endobronchial occluders or one-way valve devices ("endobronchial valves" or "EBVs") into pulmonary passageways to reduce the volume of one or more hyperinflated lung compartments, thus allowing healthier compartments more room to breathe and perhaps reducing pressure on the heart. Examples of such a method and implant are described, for example, in U.S. patent application Ser. No. 11/682,986 and U.S. Pat. No. 7,798,147, the full disclosures of which are hereby incorporated by reference. One-way valves implanted in airways leading to a lung compartment restrict air flow in the inhalation direction and allow air to flow out of the lung compartment upon exhalation, thus causing the adjoining lung compartment to collapse over time. Occluders block both inhalation and exhalation, also causing lung collapse over time.

It has been suggested that the use of endobronchial implants for lung volume reduction might be most effective when applied to lung compartments which are not affected by collateral ventilation. Collateral ventilation occurs when air passes from one lung compartment to another through a collateral channel rather than the primary airway channels. If collateral airflow channels are present in a lung compartment, implanting a one-way valve or occluder might not be as effective, because the compartment might continue to fill with air from the collateral source and thus fail to collapse as intended. In many cases, COPD manifests itself in the formation of a large number of collateral channels caused by rupture of alveoli due to hyperinflation, or by destruction and weakening of alveolar tissue.

An endobronchial catheter-based diagnostic system typically used for collateral ventilation measurement is disclosed in U.S. Patent Publication No. 2003/0051733 (hereby incorporated by reference), wherein the catheter uses an occlusion member to isolate a lung compartment and the instrumentation is used to gather data such as changes in pressure and volume of inhaled/exhaled air. Methods for collateral ventilation measurement are disclosed in U.S. Pat. No. 7,883,471 and U.S. Patent Publication Nos. 2008/0027343, 2014/0336484, and 2007/0142742 (all of which are hereby incorporated by reference), in which an isolation catheter is used to isolate a target lung compartment and pressure changes therein are sensed to detect the extent of collateral ventilation. The applications also disclose measurement of gas concentrations to determine the efficiency of gas exchange within the lung compartment. Similar methods are disclosed in PCT Application No. WO2009135070A1 (hereby incorporated by reference), wherein gas concentration changes in a catheter-isolated lung portion allow collateral ventilation to be determined.

Quantifying collateral ventilation via collateral resistance measurement and calculations typically takes about two to five minutes. During this time, the physician must ensure the patient is tolerating sedation, manage secretions to prevent occlusion within the catheter lumen, and maintain balloon seal/position within the target airway. Any one of these factors may extend the assessment time and compromise the assessment results. Thus, there is a need to quantify the magnitude of collateral ventilation within a lung compartment (lobe, segment, sub-segment, or the like) more quickly and efficiently.

Therefore, it would be advantageous to have new diagnostic techniques for evaluating the state of lung disease progression, such as determining the presence and degree of collateral ventilation. At least some of these objectives will be met by the embodiments described herein.

BRIEF SUMMARY OF THE INVENTION

This application discloses methods and systems for determining collateral ventilation in a patient. In one aspect, a method of determining collateral ventilation comprises introducing a diagnostic catheter into a lung segment via an assisted ventilation device, inflating the occluding member to isolate the lung segment, and performing a diagnostic procedure with the catheter while the patient is ventilated via the assisted ventilation device. The diagnostic catheter comprises a distal end comprising an occluding member and a proximal end configured to be attached to a console. Data generated from the diagnostic procedure may be displayed on the console. In an embodiment, the diagnostic procedure comprises determining an exhaled volume from the isolated lung segment over a predetermined period of time while the patient is ventilated via the assisted ventilation device and determining whether collateral ventilation is present in the isolated lung segment based on the exhaled volume from the isolated lung segment over the predetermined period of time. Determining whether collateral ventilation is present in the isolated lung segment may comprise determining that no collateral ventilation is present if the exhaled volume from the isolated lung segment over the predetermined period of time decreases below a threshold value. Determining whether collateral ventilation is present in the isolated lung segment may comprise determining that collateral ventilation is present if the exhaled volume from the isolated lung segment over the predetermined period of time plateaus above a threshold value. In an embodiment, a degree of collateral ventilation may be determined based on the exhaled volume from the isolated lung segment over the predetermined period of time at the plateau.

Further aspects and embodiments of the present invention are described in further detail below, in reference to the attached drawings.

BRIEF DESCRIPTION OF THE DRAWINGS

Present embodiments have other advantages and features which will be more readily apparent from the following detailed description and the appended claims, when taken in conjunction with the accompanying drawings, in which:

DETAILED DESCRIPTION OF THE INVENTION

Figure 1:
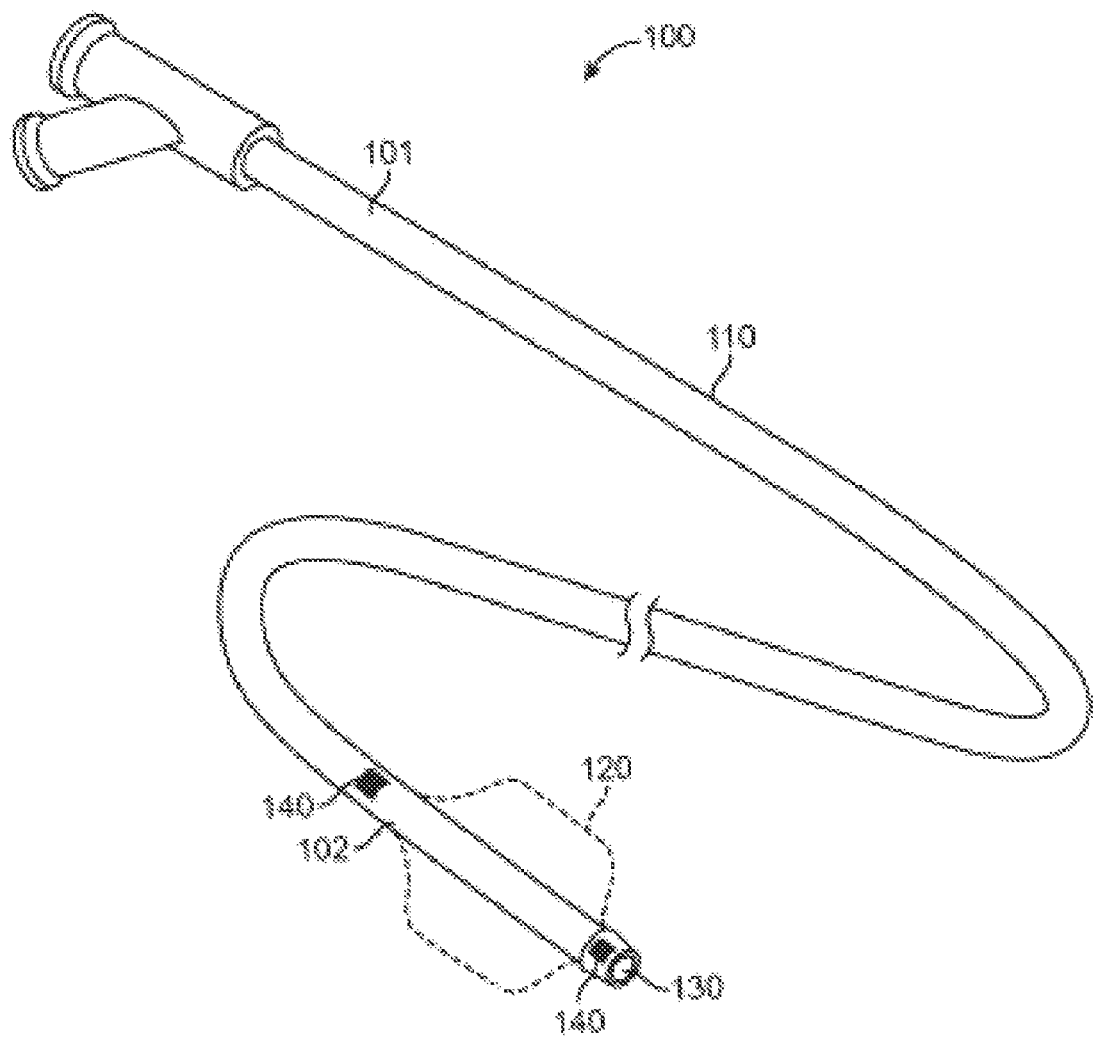
FIG. 1 shows a diagnostic or assessment catheter used in the disclosed methods according to some embodiments of the present invention.

Although the detailed description contains many specifics, these should not be construed as limiting the scope of the disclosure but merely as illustrating different examples and aspects of the disclosure. It should be appreciated that the scope of the disclosure includes other aspects and embodiments not discussed herein. Various other modifications, changes and variations which will be apparent to those skilled in the art may be made in the arrangement, operation and details of the method, device, and system of the aspects and embodiments disclosed herein without departing from the spirit and scope of the disclosure as described here.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

The present application provides methods and systems for targeting, accessing and diagnosing diseased lung compartments. Such compartments could be an entire lobe, a segment, a sub-segment or any such portion of the lung. Diagnosis is achieved in the disclosed embodiments by isolating a lung compartment to obtain various measurements to determine lung functionality. Though COPD is mentioned as an example, the applicability of these methods for treatment and diagnosis is not limited to COPD, but can be applicable to any lung disease.

The methods are minimally invasive in the sense that the required instruments are introduced through the mouth, a tracheostomy, or other site, typically via a bronchoscope, assisted ventilation device, or other non-surgical device passed through the mouth into the trachea and airways. In some embodiments, the patient is allowed to breathe normally during the procedures. Some embodiments may be used with assisted (or positive pressure) ventilation. The methods involve detecting the presence or characteristics (e.g., concentration or pressure) of one or more naturally occurring or introduced gases to determine the presence of collateral ventilation and/or to measure one or more other characteristics of a target lung compartment, such as oxygen saturation of tissue.

Figure 2:
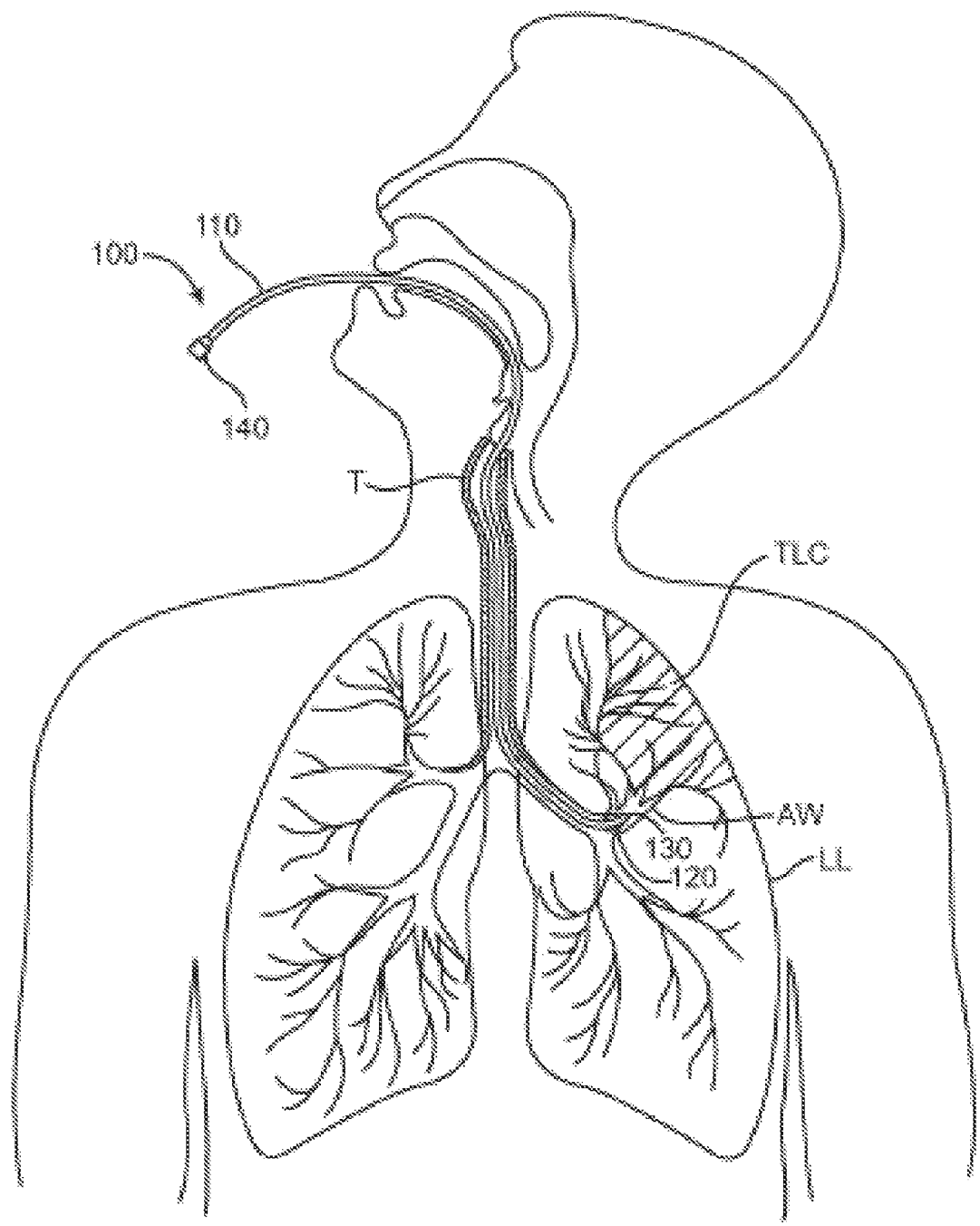
FIG. 2 shows the placement of the catheter shown in FIG. 1 in the lung.

In some of the present embodiments, isolation of the lung comprises sealingly engaging a distal end of a catheter in an airway feeding a lung compartment, as shown in FIGS. 1 and 2. Such a catheter has been disclosed in published U.S. patent application Ser. No. 10/241,733, which is incorporated herein by reference. As shown in FIG. 1, the catheter 100 comprises a catheter body 110, and an expandable occluding member 120 on the catheter body. The catheter body 110 has a distal end 102, a proximal end 101, and at least one lumen 130, extending from a location at or near the distal end to a location at or near the proximal end.

The proximal end of catheter 100 is configured to be coupled with an external control unit (or "console," not shown), and optionally comprises an inflation port (not shown). The distal end of catheter 100 is adapted to be advanced through a body passageway such as a lung airway. The expandable occluding member 120 is disposed near the distal end of the catheter body and is adapted to be expanded in the airway which feeds the target lung compartment. In one embodiment, the occluding member 120 is a compliant balloon made of transparent material. The transparent material allows visualization using the bronchoscope through the balloon. The occluding member 120 is inflatable via a syringe that is configured to be coupled to the inflation port. Optionally, catheter 100 comprises visual markers at the proximal and distal ends of the balloon to identify the location of the occluding member 120 within the airway prior to inflation. The occluding member 120 material inflates and seals with inflation pressures between 5-20 psi to prevent balloon migration within the airway. This inflation pressure also aids the occluding member 120 in maintaining a symmetrical configuration within the airway, thereby ensuring that the catheter (which is centered within the occluding member 120) will remain centered within the airway. The occluding member 120 material and attachment are also configured to minimize longitudinal movement of the occluding member 120 relative to the catheter body 110 itself. To accommodate the higher inflation pressure, the occluding member 120 is made of a polyurethane such as Pellethane 80A, but can be made of any material that is configured to maintain structural integrity at a high inflation pressure.

Additionally and optionally, catheter 100 further comprises at least one sensor 140 located within or in-line with the lumen 130 for sensing characteristics of various gases in air communicated to and from the lung compartment. The sensors may comprise any suitable sensors or any combination of suitable sensors, and are configured to communicate with control unit 200. Examples of sensors include pressure sensors, temperature sensors, air flow sensors, oxygen sensors, carbon dioxide sensors, gas-specific sensors, or other types of sensors. As shown in FIG. 1, the sensors 140 may be located near the distal end 102 of the catheter 100. Alternatively, the sensors 140 may be located at any one or more points along the catheter 100, or in-line with the catheter 100 and within the control unit with one or more measuring components.

In some embodiments the system comprises a one-way flow element located within or in-line with the lumen 130. Examples of one-way flow element are described in U.S. patent application Ser. No. 15/358,483, the full disclosure of which is hereby incorporated by reference. One-way flow elements may be configured to allow flow from an isolated lung compartment in a distal-to-proximal direction but inhibit or block flow back into the lung compartment in the proximal-to-distal direction.

As shown in FIG. 2, at least a distal portion of the catheter body 110 is adapted to be advanced into and through the trachea (T). The catheter may optionally be introduced through or over an introducing device such as a bronchoscope. The distal end 102 of the catheter body 110 can then be directed to a lung lobe (LL) to reach an airway (AW) which feeds a target lung compartment (TLC), which is to be assessed. When the occluding member 120 is expanded in the airway, the corresponding compartment is isolated with access to and from the compartment provided through the lumen 130.

Figure 3:
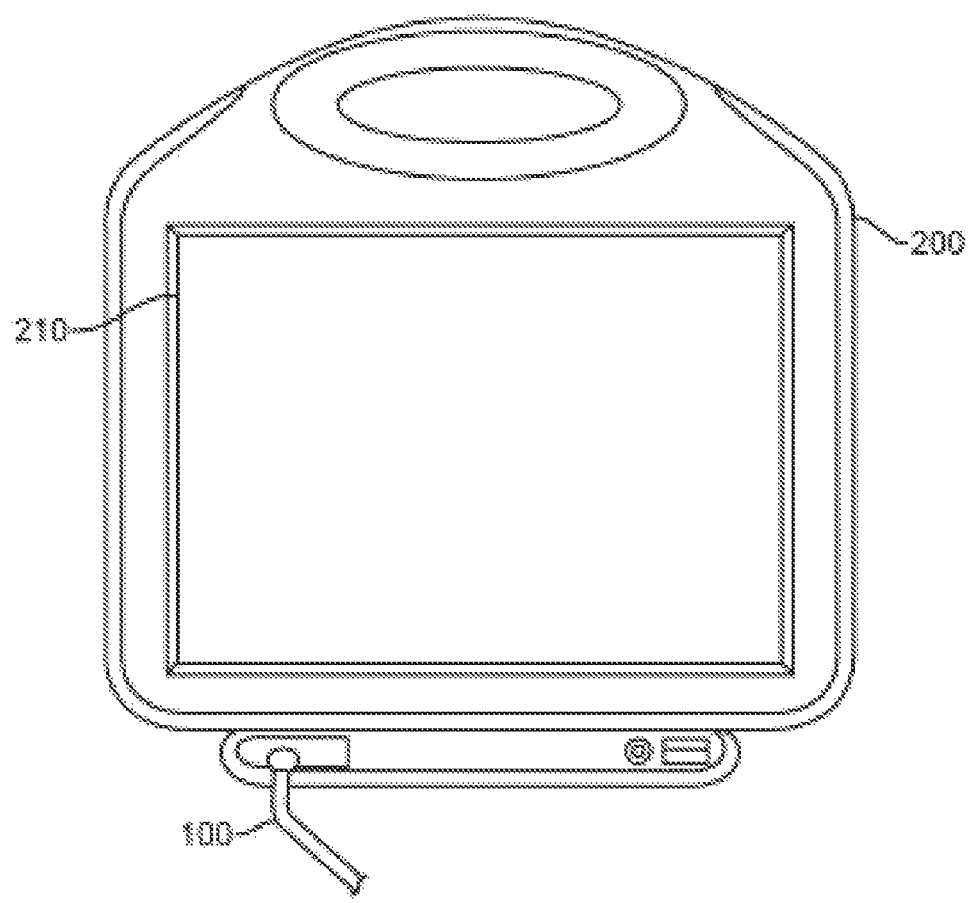
FIG. 3 shows a console configured to receive the catheter shown in FIG. 1.

The proximal end of the catheter 100 is configured to be coupled with a control unit (or "console") 200, as shown in FIG. 3. The control unit 200 comprises one or more measuring components (not shown) to measure lung functionality. The measuring components may take many forms and may perform a variety of functions. For example, the components may include a pulmonary mechanics unit, a physiological testing unit, a gas dilution unit, an imaging unit, a mapping unit, a treatment unit, a pulse oximetry unit or any other suitable unit. The components may be disposed within the control unit 200, or may be attached to the unit 200 from an external source. The control unit 200 comprises an interface for receiving input from a user and a display screen 210. The display-screen 210 will optionally be a touch-sensitive screen, and may display preset values. Optionally, the user will input information into the control unit 200 via a touch-sensitive screen mechanism. Additionally and optionally, the control unit 200 may be associated with external display devices such as printers or chart recorders. At least some of the above system embodiments will be utilized in the methods described below.

Figure 4:
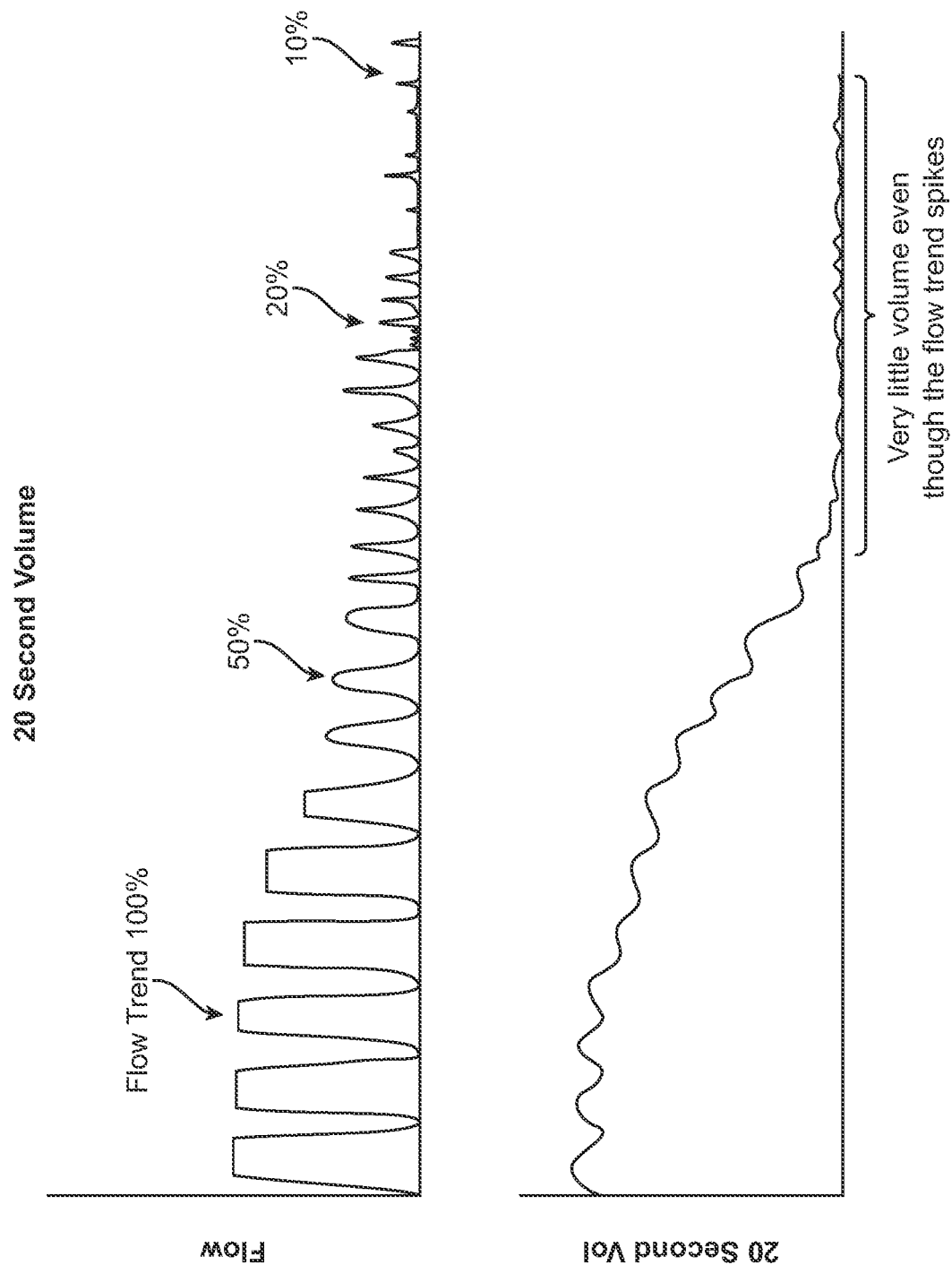
FIG. 4 shows flow and volume illustrating one embodiment of the present invention.

FIG. 4 shows flow and volume illustrating one embodiment of the present invention for determining whether collateral ventilation is present based on exhaled volume over a predetermined time. In an embodiment a diagnostic catheter is introduced into a lung compartment via an assisted ventilation device, inflating the occluding member to isolate the lung compartment, and performing a diagnostic procedure with the catheter while the patient is ventilated via the assisted ventilation device. Data generated from the diagnostic procedure may be displayed on a console. In an embodiment, the diagnostic procedure comprises determining an exhaled volume from the isolated lung compartment over a predetermined period of time while the patient is ventilated via the assisted ventilation device. Exhaled volume may be determined by measuring flow and integrating to get volume. In an embodiment, the predetermined period is approximately 20 seconds. In other embodiments the predetermined period is in the range of approximately 2-60 seconds. Each data point on the volume graph represents the exhaled volume over the previous predetermined period. After the predetermined period, every second going forward clocks the amount of volume in the previous predetermined period. As can be seen in FIG. 4, if no collateral ventilation is present, the exhaled volume from the isolated lung compartment over the predetermined period of time would decrease to near 0. While there may be brief flow spikes, very little volume would be exhaled. The system may be configured to detect a lack of collateral ventilation if the exhaled volume from the isolated lung compartment over the predetermined period of time decreases below a threshold value. If collateral ventilation is present, the exhaled volume from the isolated lung compartment over the predetermined period of time would plateau and remain relatively flat at the leak rate. The system may be configured to detect the collateral ventilation if the exhaled volume from the isolated lung compartment over the predetermined period of time plateaus above a threshold value. In an embodiment, a degree of collateral ventilation may be determined based on the exhaled volume from the isolated lung compartment over the predetermined period of time at the plateau. A higher value of volume at the plateau would indicate a higher degree of collateral ventilation.

Although certain embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially.

What is claimed is:

1. A method of determining collateral ventilation in a patient, the method compromising:
   introducing a diagnostic catheter into a lung compartment via an assisted ventilation system, wherein the diagnostic catheter comprises a distal end comprising an occluding member and a proximal end configured to be attached to a console;
   inflating the occluding member to isolate the lung compartment; and
   performing a diagnostic procedure with the diagnostic catheter while the patient is ventilated via the assisted ventilation system, wherein data generated from the diagnostic procedure are displayed on the console;
   wherein the diagnostic procedure comprises determining an exhaled volume from the isolated lung compartment over a predetermined period of time while the patient is ventilated via the assisted ventilation system and determining that collateral ventilation is present in the isolated lung compartment if the exhaled volume from the isolated lung compartment over the predetermined period of time plateaus above a threshold value and remains substantially flat for a respective flow trend.

2. The method of claim 1, further comprising determining that no collateral ventilation is present if the exhaled volume from the isolated lung compartment over the predetermined period of time decreases below the threshold value.

3. The method of claim 1, further comprising determining a degree of collateral ventilation based on the exhaled volume from the isolated lung compartment over the predetermined period of time at the plateau.

4. The method of claim 3, wherein the predetermined period of time is approximately 20 seconds.

5. The method of claim 3, wherein the predetermined period of time is approximately between 2 seconds and 60 seconds.

6. The method of claim 1, wherein the console is configured to display at least a graph with a plurality of data points, each data point of the plurality of data points representing the exhaled volume from the isolated lung compartment over a previous predetermined period of time.

7. The method of claim 6, wherein the diagnostic procedure comprises determining that collateral ventilation is not present if one or more of the plurality of data points is 50% or less of a peak flow trend.

8. The method of claim 6, wherein the diagnostic procedure comprises determining that collateral ventilation is present if each data point of the plurality of data points is greater than 50% of a peak flow trend.

9. The method of claim 1, wherein the exhaled volume from the isolated lung compartment over the predetermined period of time remains substantially flat at a leak rate at the plateau.

10. The method of claim 1, further comprising determining that no collateral ventilation is present if the exhaled volume from the isolated lung compartment over the predetermined period of time decreases to approximately zero.

11. A system for determining collateral ventilation in a patient, the system comprising:
- a diagnostic catheter configured to be introduced into a lung compartment via an assisted ventilation system, the diagnostic catheter comprising an occluding member on a distal end configured to inflate such that the lung compartment is isolated;
- a display configured to display data generated from a diagnostic procedure performed with the diagnostic catheter while the patient is ventilated via the assisted ventilation system; and
- a control unit coupled to the diagnostic catheter, wherein the control unit is configured to:
  determine an exhaled volume from the isolated lung compartment over a predetermined period of time while the patient is ventilated via the assisted ventilation system; and
  determine that collateral ventilation is present in the isolated lung compartment if the exhaled volume from the isolated lung compartment over the predetermined period of time plateaus above a threshold value and remains substantially flat for a respective flow trend.

12. The system of claim 11, wherein the control unit is further configured to determine no collateral ventilation is present if the exhaled volume from the isolated lung compartment over the predetermined period of time decreases below the threshold value.

13. The system of claim 11, wherein the display is configured to display at least a graph with a plurality of data points, each data point of the plurality of data points representing the exhaled volume from the isolated lung compartment over a previous predetermined period of time.

14. The system of claim 13, wherein the control unit is further configured to determine that collateral ventilation is not present if one or more of the plurality of data points is 50% or less of a peak flow trend.

15. The system of claim 13, wherein the control unit is further configured to determine that collateral ventilation is present if each data point of the plurality of data points is greater than 50% of a peak flow trend.

16. The system of claim 11, wherein the control unit is further configured to determine a degree of collateral ventilation based on the exhaled volume from the isolated lung compartment over the predetermined period of time at the plateau.

17. The system of claim 16, wherein the predetermined period of time is approximately 20 seconds.

18. The system of claim 16, wherein the predetermined period of time is approximately between 2 seconds and 60 second.

19. The system of claim 11, wherein the exhaled volume from the isolated lung compartment over the predetermined period of time remains substantially flat at a leak rate at the plateau.

20. The system of claim 11, wherein the control unit is further configured to determine no collateral ventilation is present if the exhaled volume from the isolated lung compartment over the predetermined period of time decreases to approximately zero.

* * * * *